United States Patent [19]

Lalezari et al.

[11] Patent Number: 5,962,651
[45] Date of Patent: Oct. 5, 1999

[54] MODIFIED HEMOGLOBIN AND ITS USE AS A COMPONENT OF AN ARTIFICIAL BLOOD SUBSTITUTE

[75] Inventors: Iraj Lalezari; Parviz Lalezari, both of Scarsdale, N.Y.

[73] Assignee: Montefiore Medical Center, Bronx, N.Y.

[21] Appl. No.: 08/903,930

[22] Filed: Jul. 31, 1997

Related U.S. Application Data

[63] Continuation of application No. 08/380,097, Jan. 27, 1995, abandoned.
[51] Int. Cl.[6] .......................... A61K 35/14; A61K 38/16; C07C 69/76
[52] U.S. Cl. .......................... 530/385; 530/380; 530/829; 514/6; 514/832; 560/1; 560/8; 560/18; 560/27; 560/34; 560/53; 560/64
[58] Field of Search .......................... 514/6, 832; 530/380, 530/385, 829; 560/1, 8, 18, 27, 34, 53, 64

[56] References Cited

U.S. PATENT DOCUMENTS

| | | | |
|---|---|---|---|
| 5,028,588 | 7/1991 | Hoffman et al. | 514/6 |
| 5,122,539 | 6/1992 | Abraham et al. | 514/563 |
| 5,239,061 | 8/1993 | Fronticelli et al. | 530/385 |
| 5,268,500 | 12/1993 | Calezari et al. | 560/34 |

*Primary Examiner*—Cecilia J. Tsang
*Assistant Examiner*—Abdel A. Mohamed
*Attorney, Agent, or Firm*—Hedman, Gibson & Costigan, P.C.

[57] ABSTRACT

The present invention provides a chemically modified form of hemoglobin that is stabilized and can efficiently bind and release oxygen. In addition the chemically modified hemoglobin may be polymerized to increase its molecular weight and increase its stability so that it will have a longer half life in the circulatory system and may be used as a stable oxygen transport mediator which is useful as the basis of a blood substitute.

24 Claims, 15 Drawing Sheets a    X = 2-Cl; Y = S      d    X = 3-Cl; Y = S
b    X = 2-Cl; Y = SO      e    X = 3-Cl; Y = SO
c    X = 2-Cl; Y = $SO_2$      f    X = 3-Cl; Y = $SO_2$ a    X = H
b    X = Cl a  X = H
b  X = Cl a  X = 3-Cl
b  X = 2,3-Cl$_2$
c  X = 3,5-Cl$_2$ a  1,3 POSITION
b  1,4 POSITION

```
a    X = Y = H
b    X = 2Cl, Y = 3Cl
c    X = 2Cl, Y = 4Cl
d    X = 2Cl, Y = 5Cl
e    X = 3Cl, Y = 4Cl
f    X = 3Cl, Y = 5Cl
``` a: X = Y = H
b: X = H; Y = Cl
c: X = Cl; Y = H a: X = Z = H; Y = Cl
b: X = Z = Cl; Y = H
c: X = Cl; Y = Z = H a: X = CO
b: X = HCOH
c: X = CH₃COH a  n = 1
b  n = 2

FOUR DIFFERENT METHODS FOR SYNTHESIS OF UREIDOPHENOXYISOBUTYRIC ACIDS

METHOD 1

METHOD 2

METHOD 3

FINAL STEP OF METHODS 1-3

MODIFIED HEMOGLOBIN AND ITS USE AS A COMPONENT OF AN ARTIFICIAL BLOOD SUBSTITUTE

This is a continuation of application Ser. No. 08/380,097, filed Jan. 27, 1995 now abandoned.

BACKGROUND OF THE INVENTION

The well known complications of blood transfusion namely incompatibility reactions, disease transmission, immunosuppression and the storage limitations of erythrocytes points to the need for the development of blood substitutes devoid of these shortcomings. Blood substitutes will have numerous applications provided they are safe, meet the viscosity and flow requirements, have long in vivo and shelf life and are cost effective. The products currently under development include perfluorocarbons and Hb-based oxygen carriers. Each of these preparations offer advantages and disadvantages but none appears to be useful for making an artificial blood substitute.

The present invention provides a modified hemoglobin and describes the use of the modified hemoglobin as a component of a blood substitute composition. It is well known that the hemoglobin molecule is present in erythrocytes and acts as the agent for the transport of oxygen in mammalian circulatory systems by binding and releasing oxygen. Hemoglobin is a conjugated protein with an approximate molecular weight of 64,000. It contains basic proteins, the globins and ferroprotoporphyrin or heme. It is essentially a tetramer consisting of two alpha chains each containing 141 amino acids and two beta chains each containing 146 amino acids. The binding site for oxygen in each of the monomers which make up the tetramer is the $Fe^{+2}$ molecule in the heme molecule. The oxygen binding capability is modified by the presence of 2,3-di-phospho glycerate (2,3-DPG). The 2,3-DPG is reversibly attached to the central cavity of the Hb which is formed by the steric configuration of the hemoglobin molecule. It is known that when hemoglobin is separated from erythrocytes by hemolysis, it retains its ability to bind oxygen but loses its ability to readily release oxygen which is facilitated by the presence of 2,3-DPG. Even though free hemoglobin is commercially available as a genetically engineered material, its use as an oxygen carrier has not been possible because of its instability and the problem of the releasability of bound oxygen. In the blood circulation, free hemoglobin breaks down into its dimer and monomeric subunits which cannot be retained because of their relatively small size. These small fragments of hemoglobin are readily filtered by the kidneys and may pass through the subendotheilium. The fragments will also bind NO (endotheilial cell derived smooth muscle relaxing factor). The binding of NO causes elevation of the systemic and pulmonary vascular resistance.

The present invention provides a chemically modified form of hemoglobin that is stabilized and can efficiently bind and release oxygen. In addition the chemically modified hemoglobin may be polymerized to increase its molecular weight and increase its stability so that it will have a longer half life in the circulatory system and may be used as a stable oxygen transport mediator which is useful as the basis of a blood substitute. The chemical modification is achieved by the use of clofibric acid derivatives.

SUMMARY OF THE INVENTION

The present invention is directed to a modified form of hemoglobin which is prepared by reacting hemoglobin with a mono-, di-, tri- or tetrafunctional effector compound that will covalently bind to the central cavity of said hemoglobin and stabilize said hemoglobin against degradation by establishing intramolecular bridges and will modify the oxygen affinity of said hemoglobin.

Natural or mutant hemoglobin, obtained from a natural source or by genetically engineered processes, may be utilized in the practice of the invention. The compounds that may be reacted with hemoglobin are of the formulas:

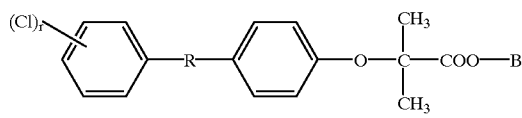

(a)

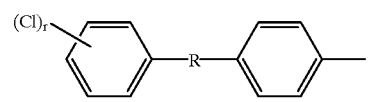

(b)

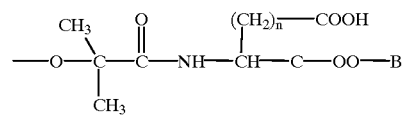

wherein R is a bond between the carbon atoms of the phenyl rings;

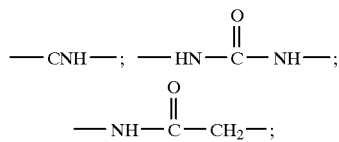

n is 1 or 2; r is 1, 2 or 3 and B is the residue of a compound having an hydroxyl group which reacts with a carboxyl group to form an active ester which reacts rapidly (instantaneously to 3 hours) with a primary amino group. These compounds include N-hydroxysuccinimide, N-hydroxysulfosuccinimide; 3,5-dibromo-salicylic acid; N-hydroxyphthalimide and the like. N-hydroxysulfosuccinimide and 3,5-dibromo-salicylic acid are the preferred compounds for the synthesis of active esters when more soluble products are desired.

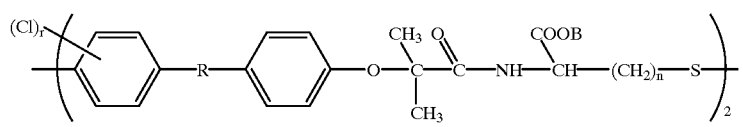

(c)

wherein R is as defined above; B is as defined above; n is 1 or 2 and r is as defined above.

(d)
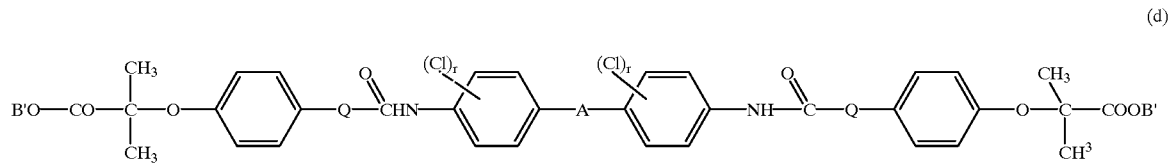

wherein A is a bond between the carbon atoms of the phenyl rings, CH$_2$;

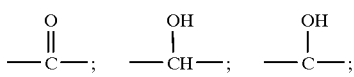

—S—;  —SO—;  —SO$_2$—;  —CH$_2$CH$_2$—; or —CH=CH—. Q is —NH—, a bond between the carbon of the phenyl ring and the carbonyl group; or —CH$_2$—; and B' is H or is the same as B which is defined above, provided that at least one B' is B, r is as defined above.

(e)
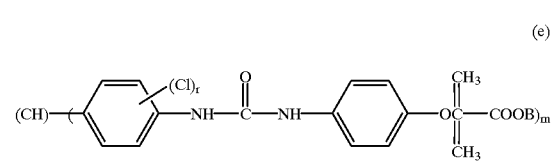

wherein B and r are as defined above and m is 3.

(f)
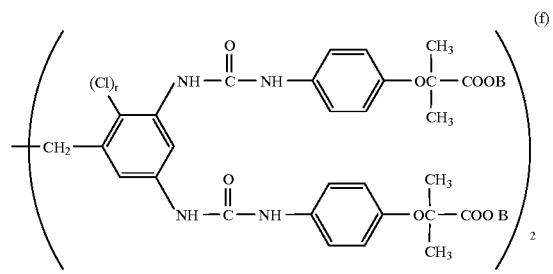

wherein B is the same as defined above.

Accordingly it is an object of the invention to provide compounds which may be used to prepare modified hemoglobin.

It is also an object of the invention to prepare a modified hemoglobin which may be used to prepare an artificial blood substitute.

DETAILED DESCRIPTION OF THE INVENTION

Some of the compounds of the invention which are used to prepare the active ester intermediates are known compounds and some are novel compounds. All of the active esters are novel compounds.

Figure 1:
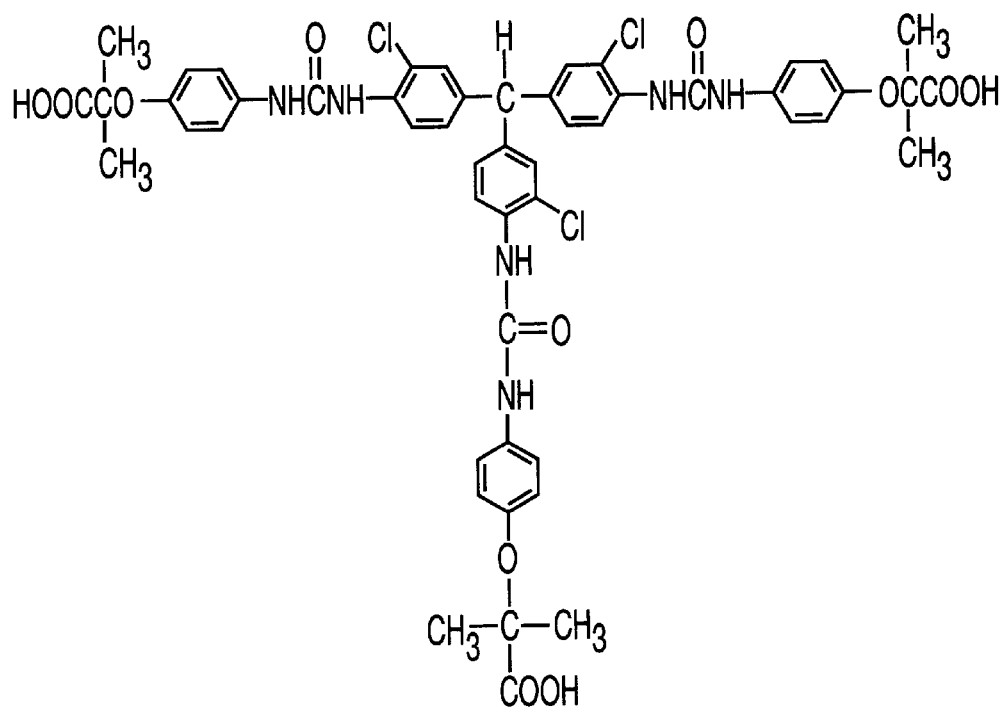
FIG. 1 is a diagram which depicts structures of compounds which may be used to prepare esters to prepare modified hemoglobin.
Figure 1:
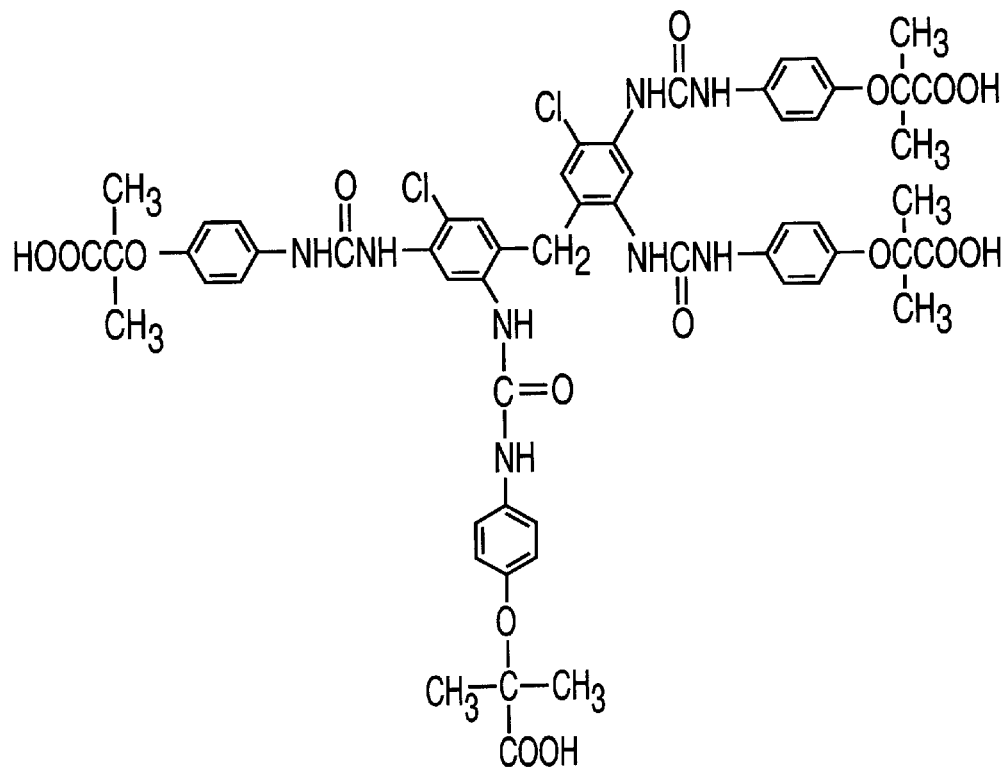
Figure 2:
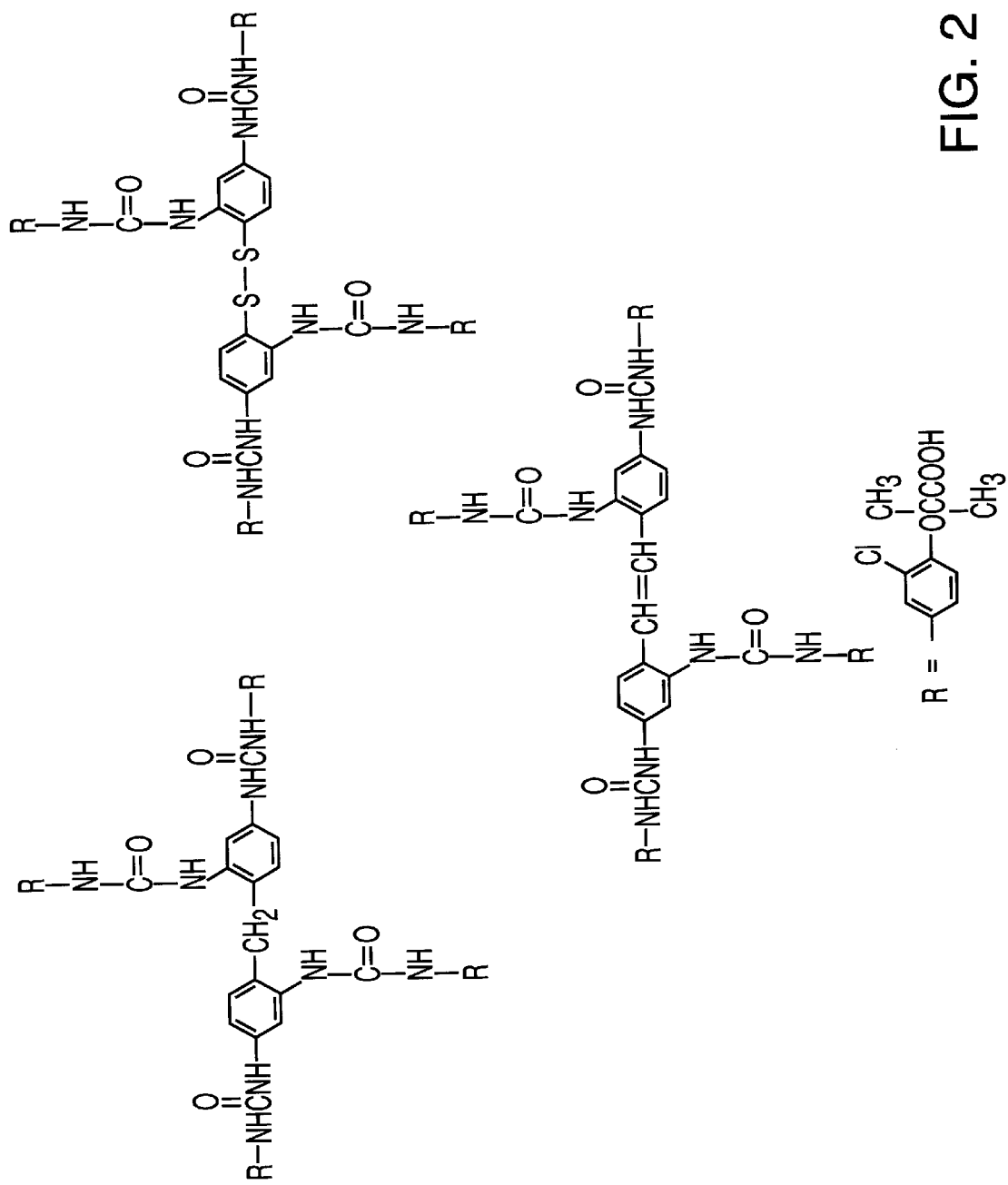
FIG. 2 is a diagram which depicts structures of compounds which may be used to prepare esters to prepare modified hemoglobin.
Figure 3:
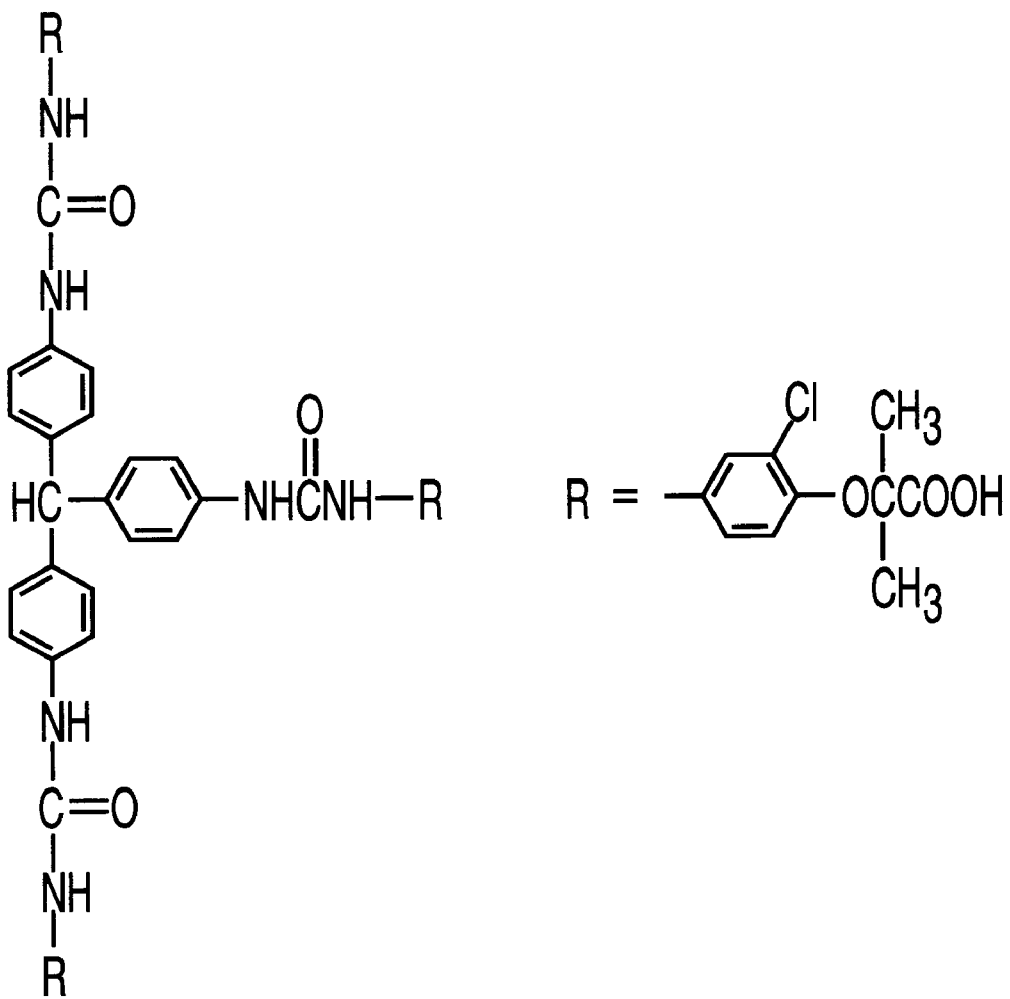
FIG. 3 is a diagram which depicts structures of compounds which may be used to prepare esters to prepare modified hemoglobin.
Figure 4:
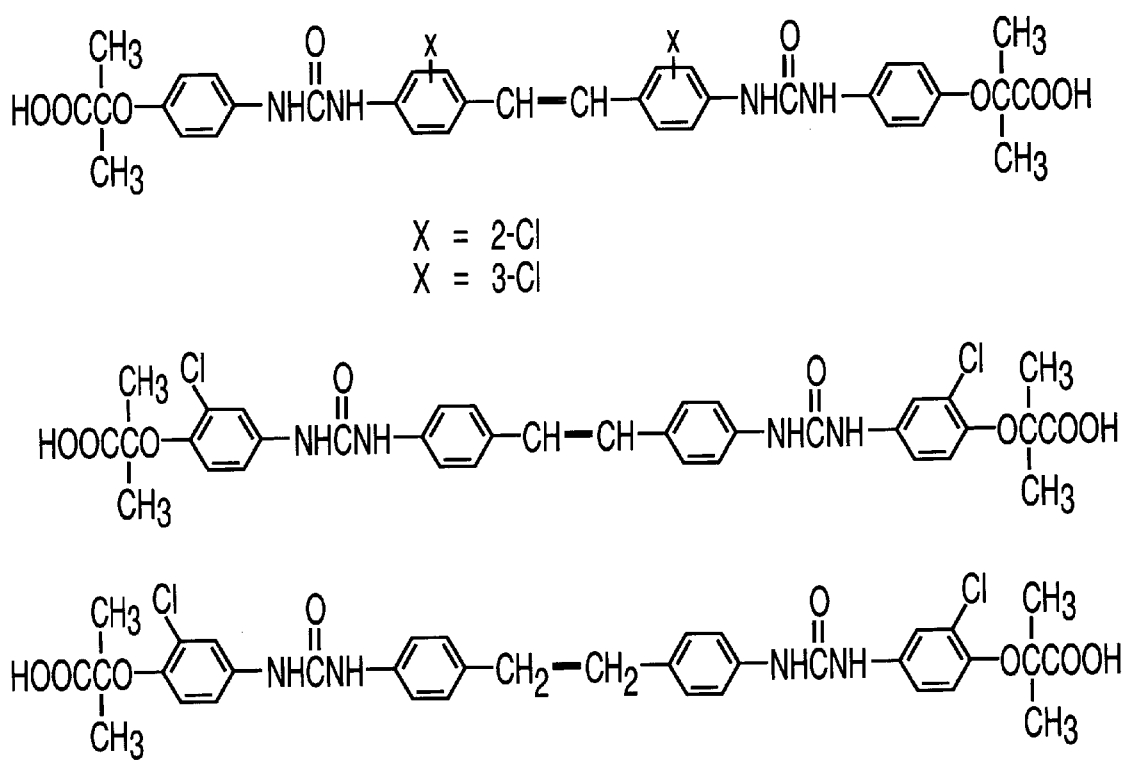
FIG. 4 is a diagram which depicts structures of compounds which may be used to prepare esters to prepare modified hemoglobin.
Figure 5:
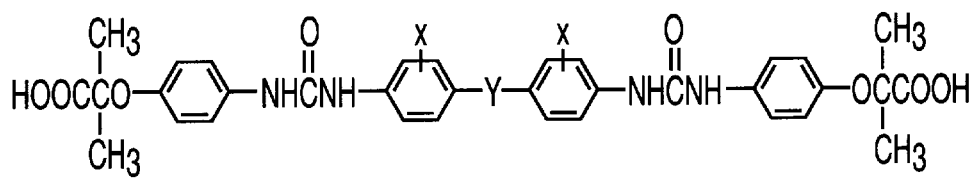
FIG. 5 is a diagram which depicts structures of compounds which may be used to prepare esters to prepare modified hemoglobin.
Figure 5:
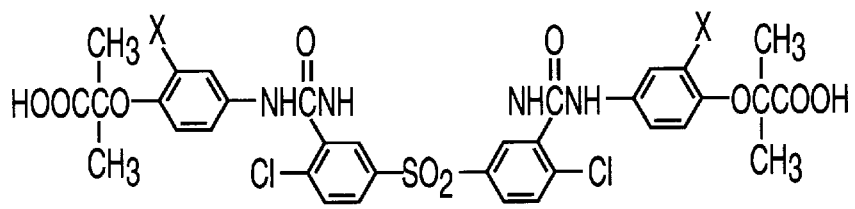
Figure 6:
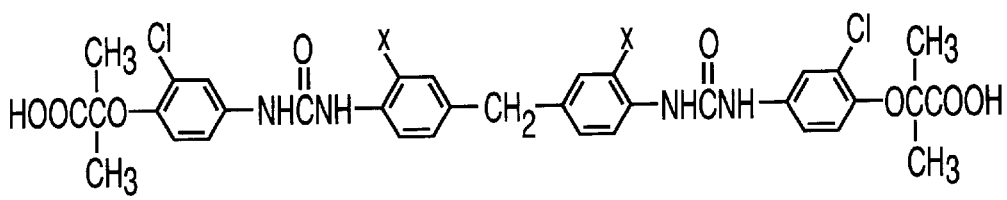
FIG. 6 is a diagram which depicts structures of compounds which may be used to prepare esters to prepare modified hemoglobin.
Figure 6:
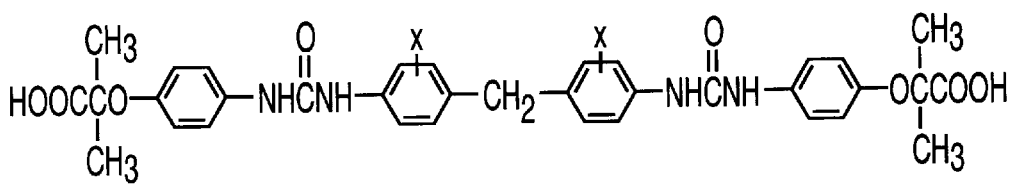
Figure 6:
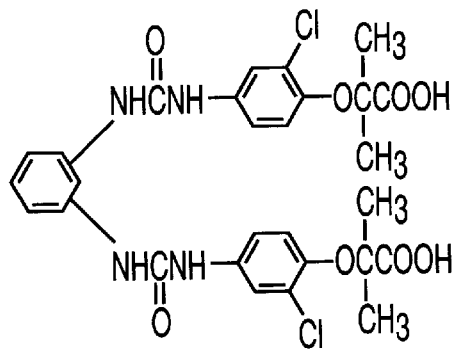
Figure 6:
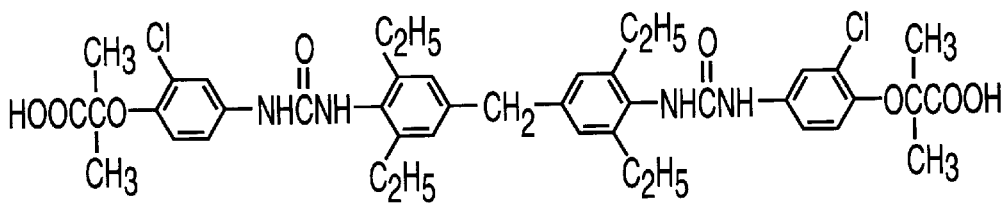
Figure 7:
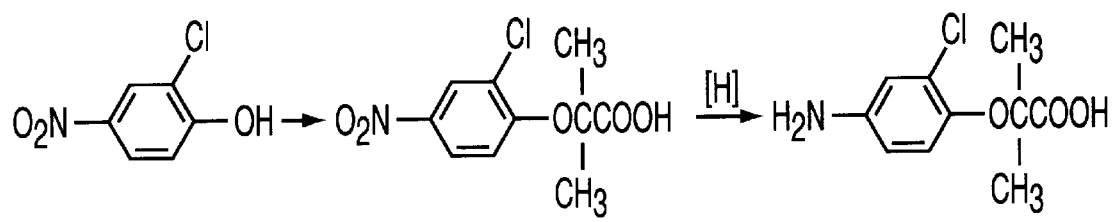
FIG. 7 is a diagram which depicts structures of compounds which may be used to prepare esters to prepare modified hemoglobin.
Figure 7:
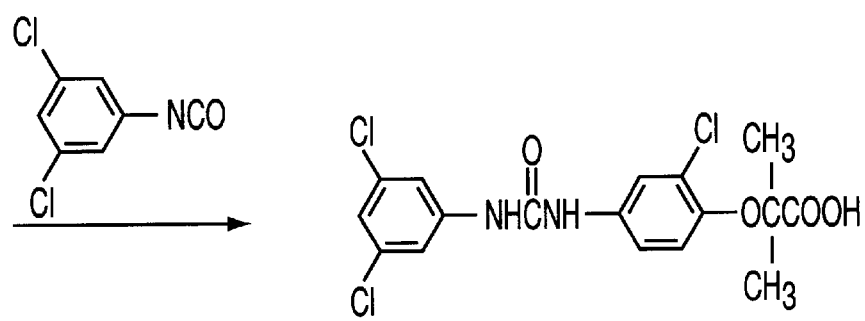
Figure 7:
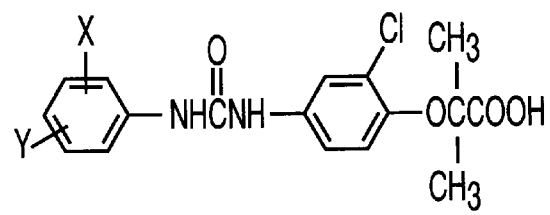
Figure 8:
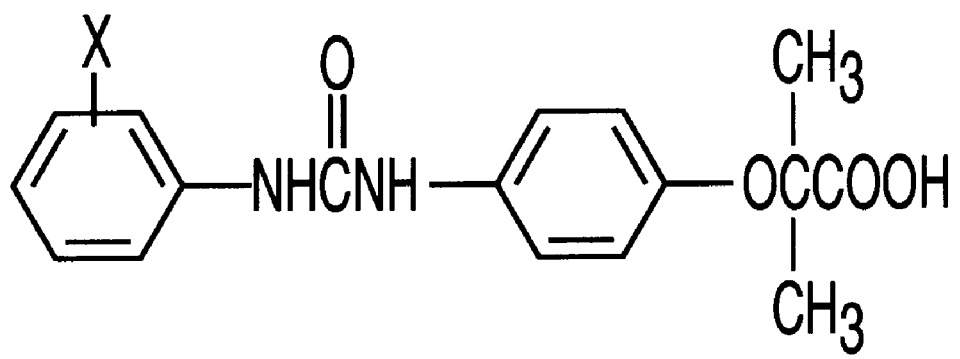
FIG. 8 is a diagram which depicts structures of compounds which may be used to prepare esters to prepare modified hemoglobin.
Figure 8:
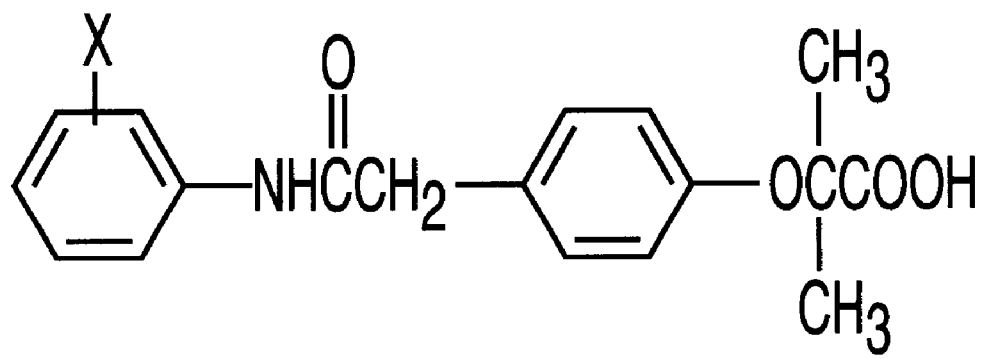
Figure 9:
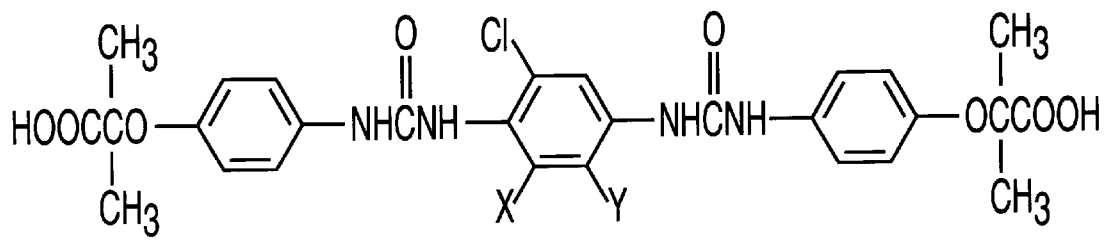
FIG. 9 is a diagram which depicts structures of compounds which may be used to prepare esters to prepare modified hemoglobin.
Figure 9:
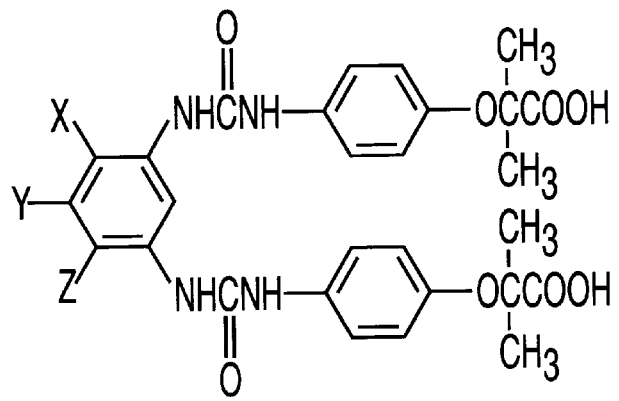
Figure 10:
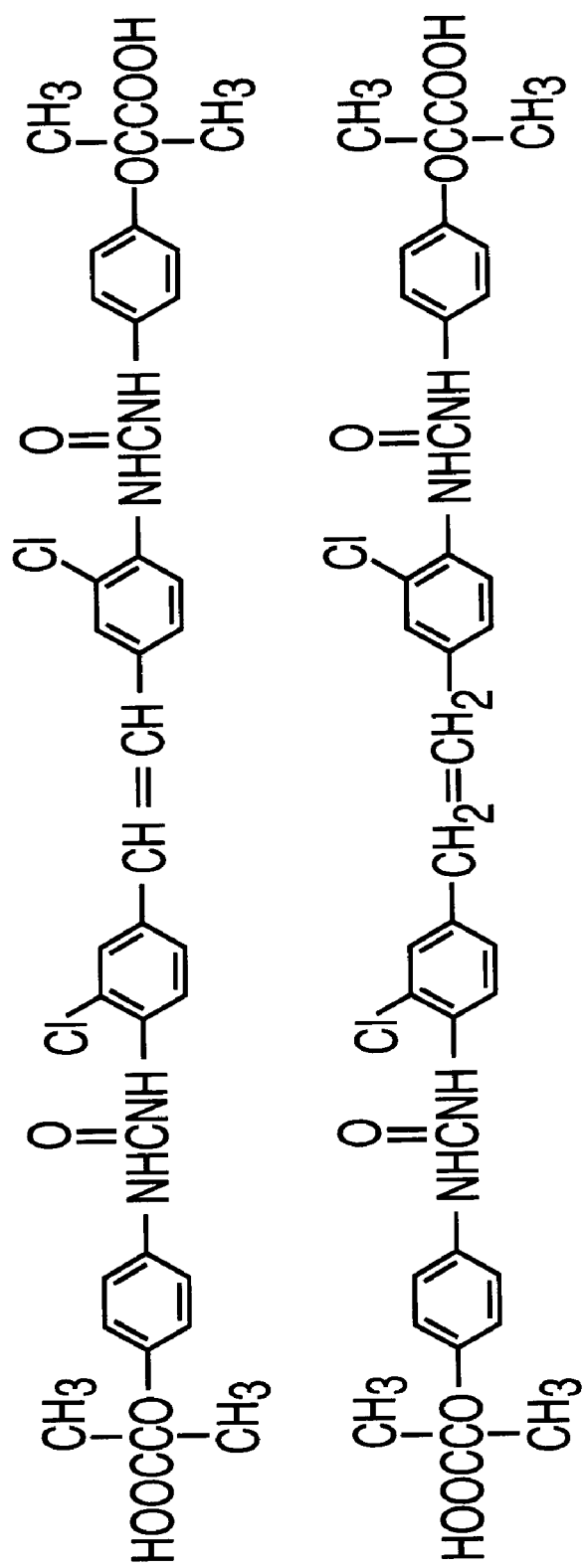
FIG. 10 is a diagram which depicts structures of compounds which may be used to prepare esters to prepare modified hemoglobin.
Figure 11:
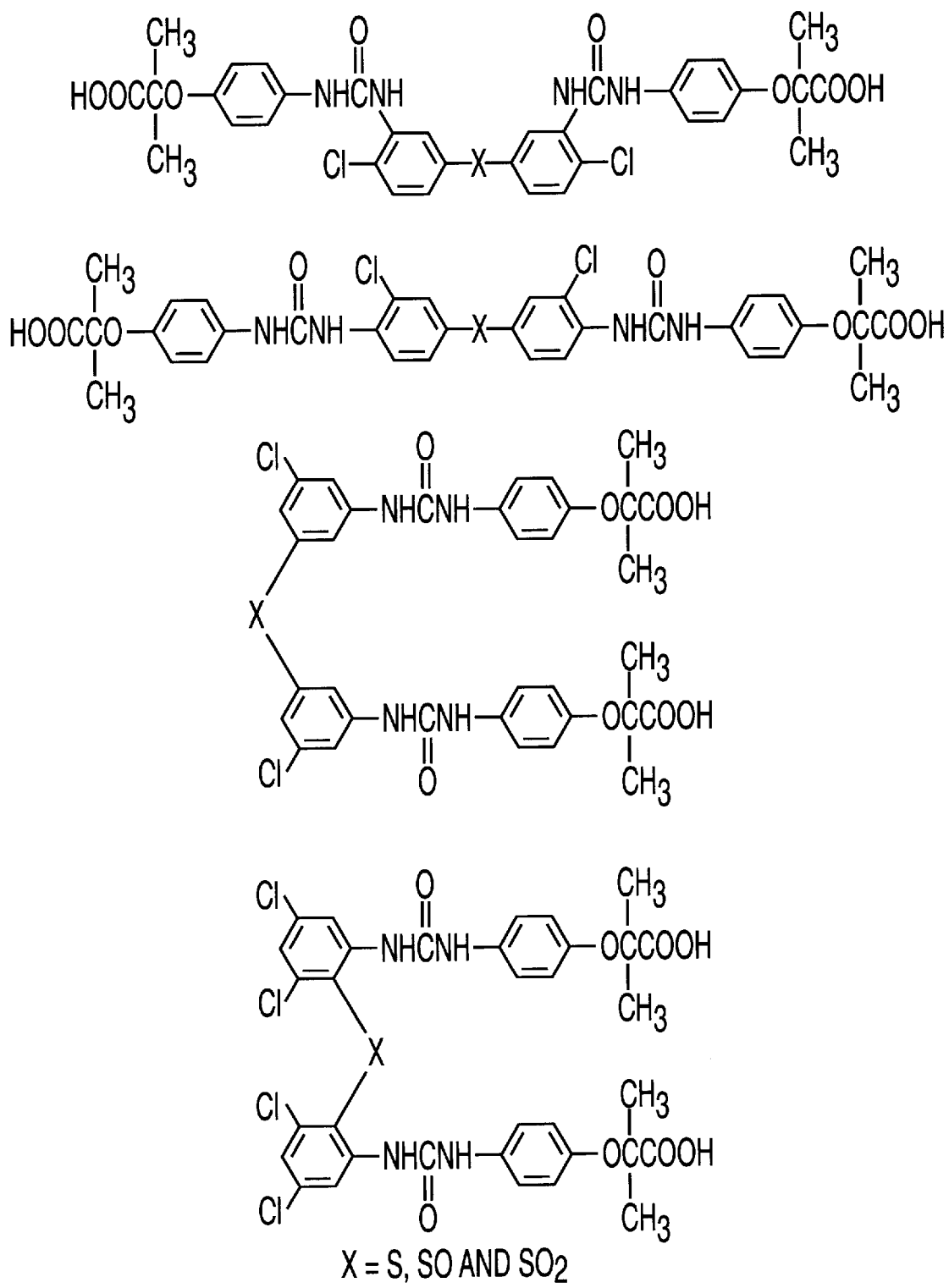
FIG. 11 is a diagram which depicts structures of compounds which may be used to prepare esters to preppare modified hemoglobin.
Figure 12:
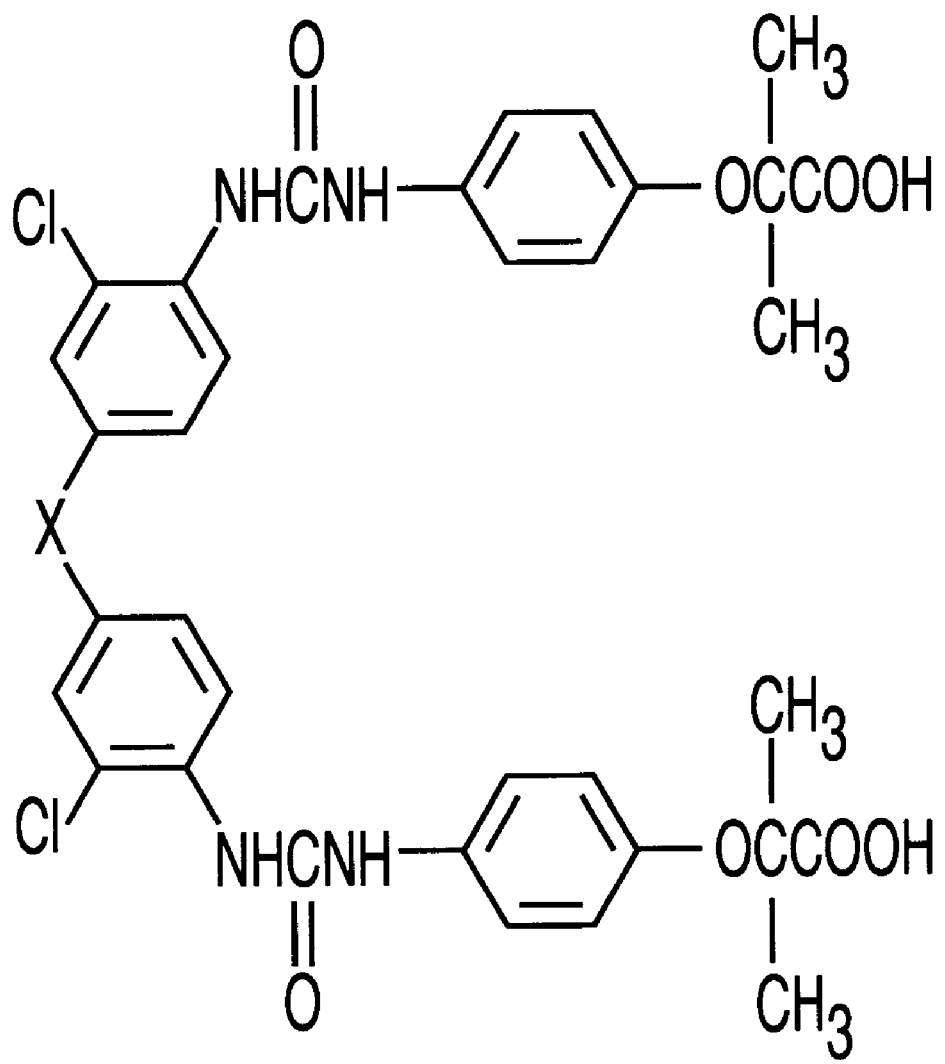
FIG. 12 is a diagram which depicts structures of compounds which may be used to prepare esters to prepare modified hemoglobin.
Figure 13:
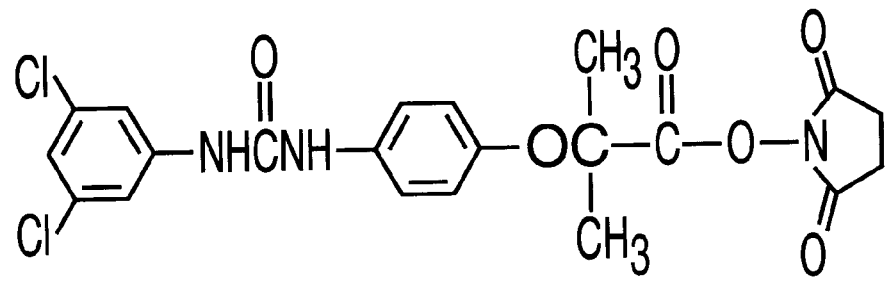
FIG. 13 is a diagram which depicts structures of compounds which may be used to prepare modified hemoglobin which have been converted into the active ester form by esterification with N-hydroxy succinimide.
Figure 13:
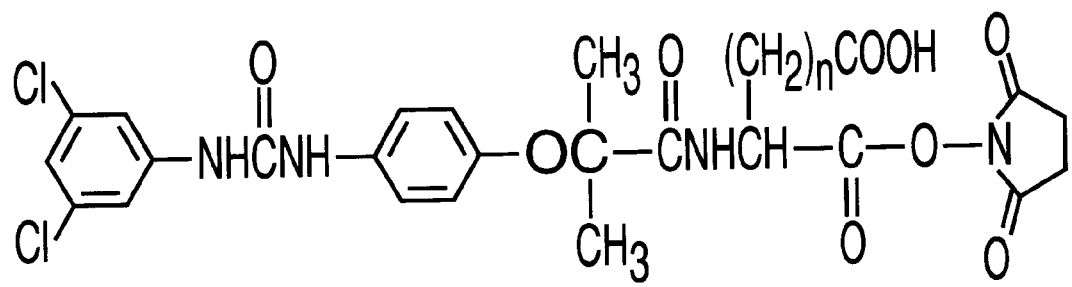
Figure 14:
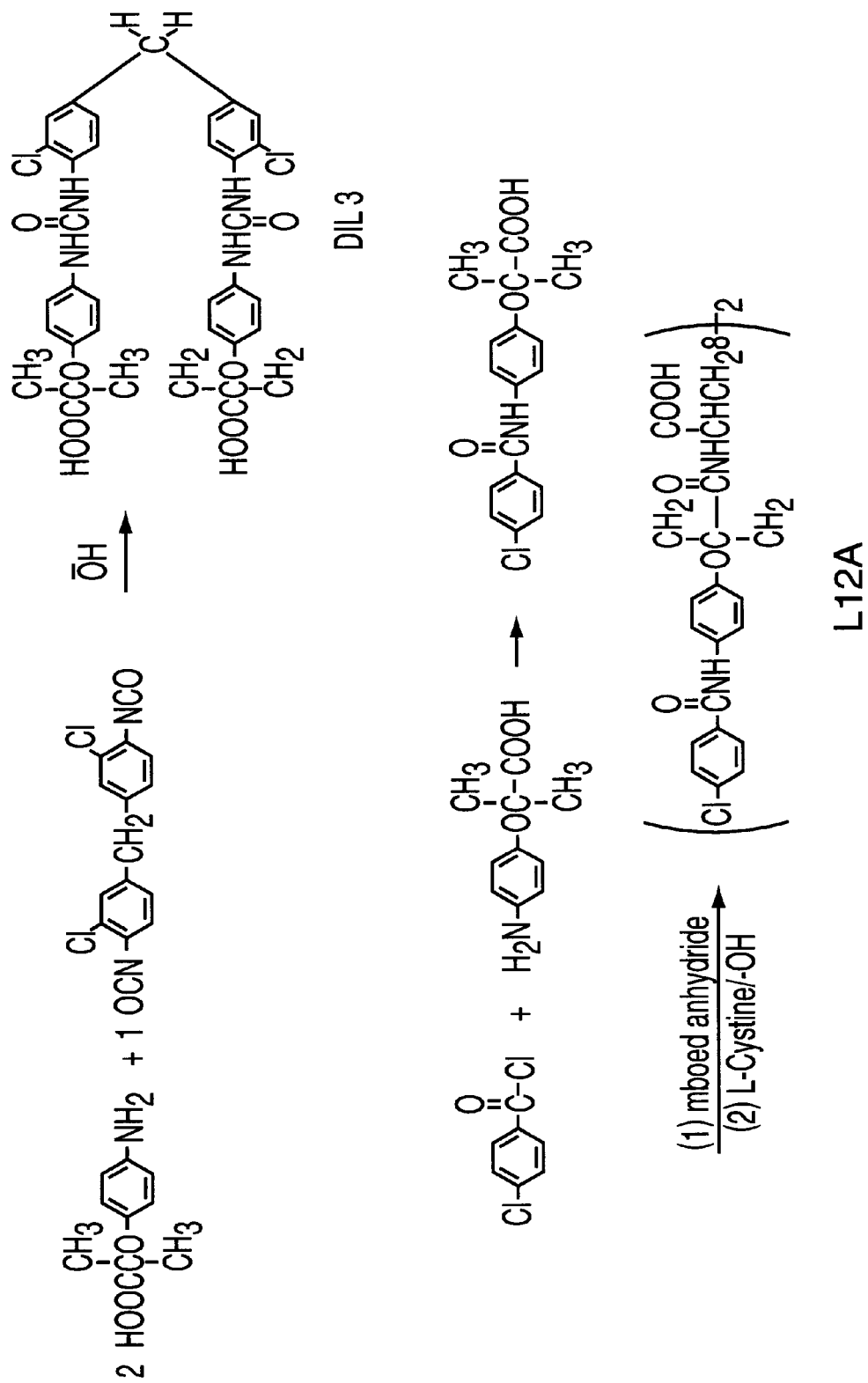
FIG. 14 is a flow sheet which shows the reactions which are used to make a difunctional compound for use in the invention.
Figure 15:
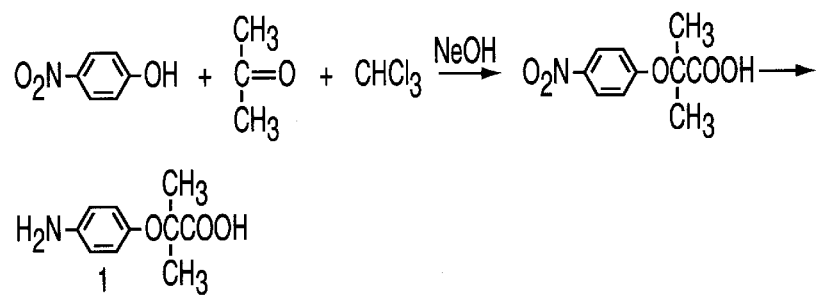
FIG. 15 is a flow sheet whioch shows four different methods of preparing compounds to make the esters of the invention.
Figure 15:
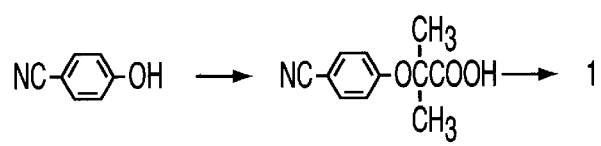
Figure 15:
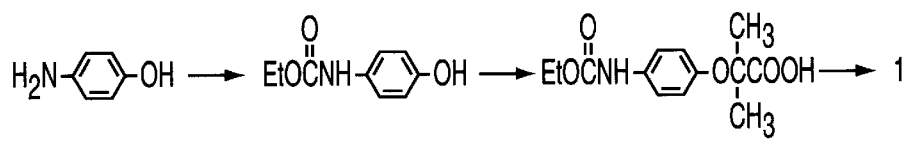
Figure 15:
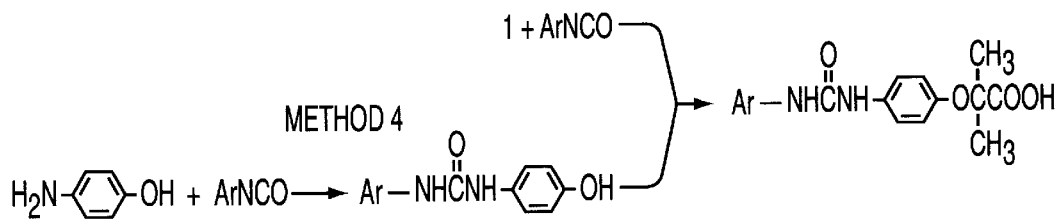

The preferred compounds of the invention are set forth in FIGS. 1–13 of the drawings and procedures for their preparation are shown in FIGS. 14–15.

Hemoglobin from any source may be reacted with the compounds of the invention to form the modified hemoglobin of the invention. Normal or mutant hemoglobins may be used as a starting material. Examples of these hemoglobins are described in Hematology, 3rd Edition, Williams et al., McGraw Hill, NY (1983), pp599–603, which is incorporated by reference. A preferred hemoglobin is Presbyterian hemoglobin, which is described in FEBS Lett.92:53 (1978)

which is incorporated by reference. Other preferred hermoglobins are mutants, naturally or genetically engineered in which additional lysine and/or arginine residues are expressed within the central cavity of the hemoglobin molecule.

Although the applicants do not wish to be bound by any theory under which the invention is based, it is believed that the compounds of the invention react with the free amino groups in the hemoglobin molecule which are present on the lysine or arginine residue. It is known that in the central cavity of hemoglobin there are lysine residues and in the case of Presbyterian hemoglobin, there is an additional lysine residue which is substituted for an asparagine residue in each beta chain. It is believed that the presence of an addition lysine residue in Presbyterian hemoglobin provides an additional binding site for the compounds of the invention.

Generally, a mole ratio from 1:1 to 20:1 of effector compound to hemoglobin is used to prepare the modified hemoglobin although this ratio may be varied depending upon the desired results. If the hemoglobin is not prepared by genetic engineering, it will be necessary to purify the hemoglobin to remove any red cell stroma or other blood components using column chromatography.

The effector compounds may be reacted with the hemoglobin by directly adding the effector compound to a solution of hemoglobin which is dissolved in a suitable buffer (e.g. 0.1M HEPES buffer at pH 7.4). After completion of the reaction, the product is purified and recovered by column chromatography free of effector compound and degraded products. The degree of binding may be ascertained by changes in the oxygen equilibrium curve in a Hemox analyzer using the procedure set forth in J. Ned. Chem, (1989) Vol. 32, No. 10, 2352, which is incorporated by reference.

In order to prepare a blood substitute composition, the modified hemoglobin of the invention is polymerized to a weight average molecular weight of about 130,000 to 10,000,000, and preferably from 500,000 to 2,000,000. The blood substitute composition may be prepared and the polymerization of the modified hemoglobin may be carried out by using glutaraldehyde or other linking agent using the procedures set forth in Sehgal et al, Surgery, 95, 433–438 (1984); Sehgal, et al., Transfusions, 23, 158–162 (1983); Tam et al. Pro. Nat. Acad. Sci. U.S.A., 73, 2128–2131 (1976); Bunn et al., Amer. J. Hematol., 42,112–117 (1993); and Bunn et al. J. Exp. Med, 129, 909–924 (1969), all of which are incorporated by reference.

The blood substitute composition may be prepared using an effective amount e.g. 7% w/v of the modified hemoglobin in an isotonic aqueous medium which may also contain conventional electrolytes. The techniques of preparing blood substitute compositions is discussed in Nance SJ Ed.,Blood Safety, Current Chalenges,Am. Assoc. of Blood Banks, Bethesda, Md. (1992) pp151–167, which is incorporated by reference.

The following Examples describe the preparation of preferred compounds of the invention.

EXAMPLE 1

To a stirring solution of N-aminophenoxyisobutyric acid, (3.9 g (0.02 mole) in 2N NaOH (5 ml in 75 ml of tetrahydrofuran cooled in an salt ice bath, is added a solution of 2.90 g. (0.01 mole) of 1,1-methylene-bis-(3-chloro-4-isocyanato) benzene in 25 ml of tetrahydrofuran, dropwise during a period of one-half hour. At the end, the stirring was continued for 1 hour at room temperature. Most of the tetrahydrofuran was removed under vacuum distillation and 2.5 ml of 2N NaOH and 25 ml of water is added and the solution decolorized by charcoal and filtration. To the filtrate, 10% sulfuric acid is added to provide a pH of 2.0. The off-white powder was filtered, washed with water and air dried. The yield is 4.5 g. (70%) mp 282–285° C. The NMR and elemental analysis is consistent with the following structure:

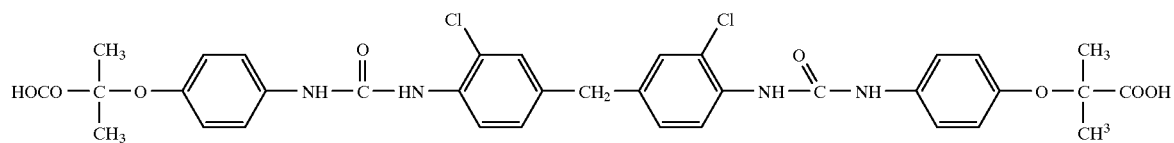

EXAMPLE 2

A mixture of 383 mg. (1 mmole) of 2-(4-(3,5-dichlorophenylureido)phenoxy)-2-methyl-propionic acid prepared according to Example 4 of U.S. Pat. No. 5,093,367 and 126 mg. (1.1 mmole) of N-hydroxysuccinimide, 26 mg. (1.1 mmole) of dicyclohexylcarbodiimide in 15 ml of tetrahydrofuran was stirred at room temperature for 4 hours, Dicyclohexylurea formed and was filtered off. The solid product was washed with 5 ml of tetrahydrofuran and evaporation under vacuum yielded 450 mg of a powder. mp 106–162° C. The NMR and elemental 2 analysis is consistent with the N-hydroxysuccinimide ester of 2-(4-(3,5-dichlorophenylureido)phenoxy)-2-methyl-propionic acid.

EXAMPLE 3

A compound of the formula:

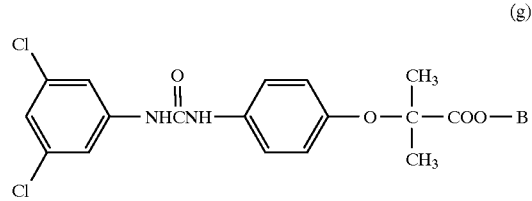

is reacted with 1 equivalent of triethylamine in tetrahydofuran and gradually 1 equivalent of ethyl chloroformate is added to yield the mixed anhydride of the compound of formula (g). One equivalent of the beta-benzyl ester of aspartic acid dissolved in 1 equivalent of 2N NaOH in water is added to the mixed anhydride with stirring over an ice bath for one-half hour. The reaction mixture is allowed to stand for 2 hours at room temperature. The product is acidified with 10% sulfuric acid and is extracted with ethyl acetate and evaporated to dryness to yield the benzyl aspartate ester of compound (g). The product is reacted with N-hydroxy phthalimide in the presence of 1 equivalent of dicyclhexylcarbodiimide. The product is extracted and hydrogenated in methanol over 5% Pd-carbon at 60 psi for 2 hours. The benzyl group is removed to yield the free acid. Glutamic acid derivatives may be prepared similiarly using one equivalent of gamma benzyl glutamic acid instead of the beta benzyl ester of gamma aspartic acid:

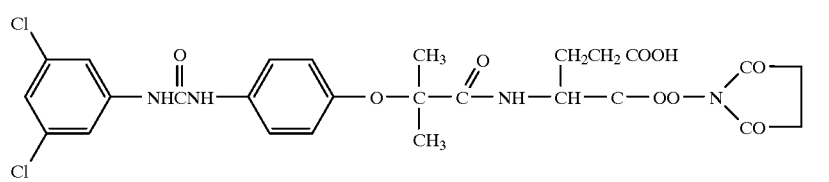

(b)

We claim:

1. Hemoglobin which is modified by reaction with a compound of the formula:

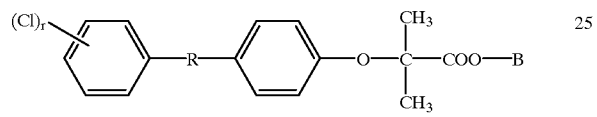

(a)

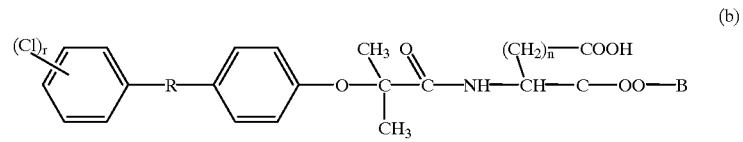

(b)

wherein R is a bond between the carbon atoms of the phenyl rings; —CNH—;

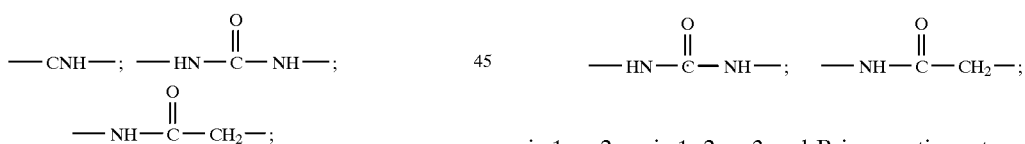

r is 1, 2 or 3 and B is an active ester moiety capable of reacting with the amino group of a hemoglobin, said active ester moiety being derived from a compound selected from the group consisting of N-hydroxysuccinimide, N-hydroxysulfosuccinimide, N-hydroxyphthalimide and 3,5-dibromosalicylic acid.

2. A blood substitute composition which comprises an effective amount of the modified hemoglobin of claim 1 and an aqueous medium.

3. A modified hemoglobin as defined in claim 1 where the hemoglobin is a mutant hemoglobin where at least one amino acid of the hemoglobin molecule in the central cavity of said hemoglobin molecule is replaced with a lysine or arginine residue.

4. A modified hemoglobin as defined in claim 3 where the hemoglobin is Presbyterian hemoglobin.

5. Hemoglobin which is modified by reaction with a compound of the formula:

wherein R is a bond between the carbon atoms of the phenyl rings; —CNH—;

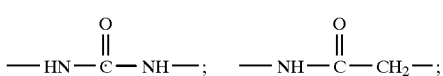

n is 1 or 2 ; r is 1, 2 or 3 and B is an active ester moiety capable of reacting with the amino group of a hemoglobin said active ester moiety being derived from a compound selected from the group consisting of N-hydroxysuccinimide, N-hydroxysulfosuccinimide, N-hydroxyphthalimide and 3,5-dibromosalicylic acid.

6. A blood substitute composition which comprises an effective amount of the modified hemoglobin of claim 5 and an aqueous medium.

7. A modified hemoglobin as defined in claim 5 where the hemoglobin is a mutant hemoglobin where at least one amino acid of the hemoglobin molecule in the central cavity of said hemoglobin molecule is replaced with a lysine or arginine residue.

8. A modified hemoglobin as defined in claim 7 where the hemoglobin is Presbyterian hemoglobin.

9. Hemoglobin which is modified by reaction with a compound of the formula:

(C)

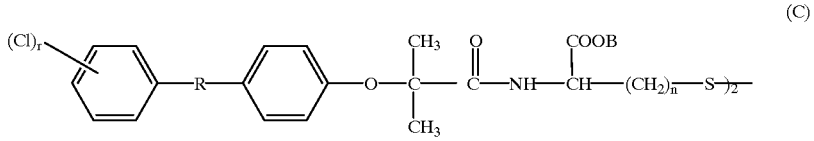

wherein R is a bond between the carbon atoms of the phenyl rings; —CNH—;

n is 1 or 2; r is 1, 2 or 3 and B is an active ester moiety capable of reacting with the amino group of a hemoglobin, said active ester moiety being derived from a compound selected from the group consisting of N-hydroxysuccinimide, N-hydroxysulfosuccinimide, N-hydroxyphthalimide and 3,5-dibromosalicylic acid.

10. A blood substitute composition which comprises an effective amount of the modified hemoglobin of claim 9 and an aqueous medium.

11. A modified hemoglobin as defined in claim 9 where the hemoglobin is a mutant hemoglobin where at least one amino acid of the hemoglobin molecule in the central cavity of said hemoglobin molecule is replaced with a lysine or arginine residue.

12. A modified hemoglobin as defined in claim 11 where the hemoglobin is Presbyterian hemoglobin.

13. Hemoglobin which is modified by reaction with a compound of the formula:

amino acid of the hemoglobin molecule in the central cavity of said hemoglobin molecule is replaced with a lysine or arginine residue.

16. A modified hemoglobin as defined in claim 15 where the hemoglobin is Presbyterian hemoglobin.

17. Hemoglobin which is modified by reaction with a compound of the formula:

(e)

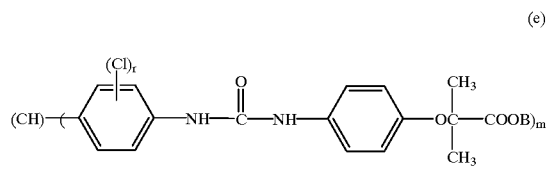

wherein B is an active ester moiety capable of reacting with the amino group of a hemoglobin, said active ester moiety being derived from a compound selected from the group consisting of N-hydroxysuccinimide, N-hydroxysulfosuccinimide, N-hydroxyphthalimide and 3,5 dibromosalicylic acid and r is 1, 2 or 3; and m is 3.

18. A blood substitute composition which comprises an effective amount of the modified hemoglobin of claim 7 and an aqueous medium.

19. A modified hemoglobin as defined in claim 17 where the hemoglobin is a mutant hemoglobin where at least one (d)

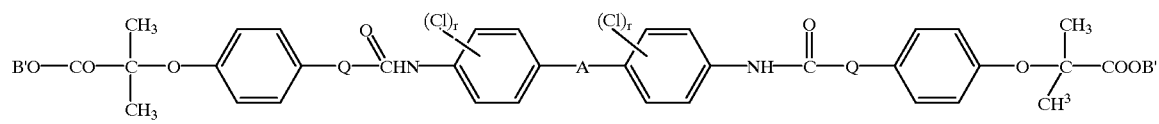

wherein A is a bond between the carbon atoms of the phenyl rings, $CH_2$;

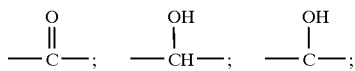

—S—; —SO—; —SO$_2$—; —CH$_2$CH$_2$—; or —CH=CH—. Q is —NH—, a bond between the carbon of the phenyl ring and the carbonyl group; or —CH$_2$—; and B' is H or is the same as B provided that at least one B' is B, r is 1, 2 or 3 and B is an active ester moiety capable of reacting with the amino group of a hemoglobin, said active ester moiety being derived from a compound selected from the group consisting of N-hydroxysuccinimide, N-hydroxysulfosuccinimide, N-hydroxyphthalimide and 3,5-dibromosalicylic acid.

14. A blood substitute composition which comprises an effective amount of the modified hemoglobin of claim 13 and an aqueous medium.

15. A modified hemoglobin as defined in claim 13 where the hemoglobin is a mutant hemoglobin where at least one amino acid of the hemoglobin molecule in the central cavity of said hemoglobin molecule is replaced with a lysine or arginine residue.

20. A modified hemoglobin as defined in claim 19 where the hemoglobin is Presbyterian hemoglobin.

21. Hemoglobin which is modified by reaction with a compound of the formula:

(f)

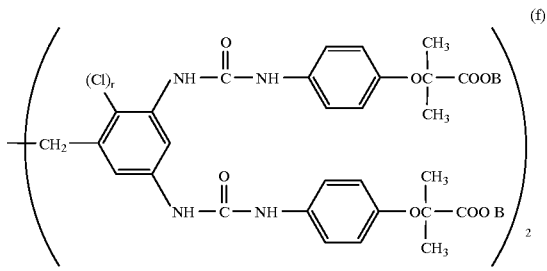

wherein B is an active ester moiety capable of reacting with the amino group of a hemoglobin, said active ester moiety being derived from a compound selected from the group consisting of N-hydroxysuccinimide, N-hydroxysulfosuccinimide, N-hydroxyphthalimide and 3,5 dibromosalicylic acid and r is 1, 2 or 3.

22. A blood substitute composition which comprises an effective amount of the modified hemoglobin of claim 2 and an aqueous medium.

23. A modified hemoglobin as defined in claim 21 where the hemoglobin is a mutant hemoglobin where at least one amino acid of the hemoglobin molecule in the central cavity of said hemoglobin molecule is replaced with a lysine or arginine residue.

24. A modified hemoglobin as defined in claim 23 where the hemoglobin is Presbyterian hemoglobin.

* * * * *